(12) United States Patent
Yamamoto et al.

(10) Patent No.: US 8,050,771 B2
(45) Date of Patent: Nov. 1, 2011

(54) PHASED ARRAY COFIRE ANTENNA STRUCTURE AND METHOD FOR OPERATING THE SAME

(75) Inventors: Joyce K. Yamamoto, Maple Grove, MN (US); Charles S. Farlow, Eden Prairie, MN (US)

(73) Assignee: Medtronic, Inc., Minneapolis, MN (US)

( * ) Notice: Subject to any disclaimer, the term of this patent is extended or adjusted under 35 U.S.C. 154(b) by 529 days.

(21) Appl. No.: 12/344,980

(22) Filed: Dec. 29, 2008

(65) Prior Publication Data

US 2010/0168817 A1   Jul. 1, 2010

(51) Int. Cl.
*A61N 1/08* (2006.01)

(52) U.S. Cl. .......................... 607/60; 607/62

(58) Field of Classification Search .................. None
See application file for complete search history.

(56) References Cited

U.S. PATENT DOCUMENTS

| | | | |
|---|---|---|---|
| 5,023,624 A | 6/1991 | Heckaman et al. | |
| 5,198,824 A | 3/1993 | Poradish | |
| 5,219,377 A | 6/1993 | Poradish | |
| 5,387,888 A | 2/1995 | Eda et al. | |
| 5,620,476 A | 4/1997 | Truex et al. | |
| 6,107,227 A | 8/2000 | Jacquin et al. | |
| 6,320,547 B1 | 11/2001 | Fathy et al. | |
| 6,391,082 B1 | 5/2002 | Holl | |
| 6,414,835 B1 | 7/2002 | Wolf et al. | |
| 6,556,169 B1 | 4/2003 | Fukuura et al. | |
| 6,580,402 B2 | 6/2003 | Navarro et al. | |
| 7,012,327 B2 | 3/2006 | Huff et al. | |
| 7,122,891 B2 | 10/2006 | Dishongh | |
| 7,164,572 B1 | 1/2007 | Burdon et al. | |
| 7,289,063 B2 | 10/2007 | Zaghloul | |
| 7,317,946 B2 | 1/2008 | Twetan et al. | |
| 7,392,015 B1 | 6/2008 | Farlow et al. | |
| 2004/0106967 A1 | 6/2004 | Van Arx et al. | |
| 2005/0109453 A1 | 5/2005 | Jacobson et al. | |

(Continued)

FOREIGN PATENT DOCUMENTS

EP     1362614 A1     11/2003
(Continued)

OTHER PUBLICATIONS

Caiazzo, et al., A Metamaterial Surface for Compact Cavity Resonators, IEEE AP Letters, 2004, pp. 261-264, vol. 3.

(Continued)

*Primary Examiner* — Kennedy Schaetzle
(74) *Attorney, Agent, or Firm* — Stephen W. Bauer; Michael J. Ostrom

(57) ABSTRACT

An antenna structure for an implantable medical device (IMD) is provided that includes an antenna embedded within a structure derived from a plurality of discrete dielectric layers. An array of electrodes are connected to the antenna structure and arranged for applying a bias across selected segments of the dielectric layers for altering the performance characteristics of the antenna. The bias applied by the array of electrodes can be selected to provide desired impedance matching between the antenna and the surrounding environment of the implant location to mitigate energy reflection effects at the transition from the antenna structure to the surrounding environment, to provide beam steering functionality for the antenna, or to alter the gain of the signals received by the antenna. IMD is configured to monitor received signal characteristics (e.g., RSSI, EVM or bit error rate) and alter material properties of the dielectric material through biasing to control antenna performance.

22 Claims, 8 Drawing Sheets

U.S. PATENT DOCUMENTS

| | | | |
|---|---|---|---|
| 2006/0212096 A1 | 9/2006 | Stevenson | |
| 2006/0214855 A1 | 9/2006 | Harada | |
| 2007/0200706 A1 | 8/2007 | Lee | |
| 2007/0236861 A1 | 10/2007 | Burdon et al. | |
| 2007/0288066 A1 | 12/2007 | Christman et al. | |
| 2008/0021522 A1 | 1/2008 | Verhoef et al. | |
| 2010/0109966 A1* | 5/2010 | Mateychuk et al. | 343/841 |
| 2010/0141360 A1* | 6/2010 | Betts-LaCroix | 333/24 C |

FOREIGN PATENT DOCUMENTS

| | | |
|---|---|---|
| EP | 1508940 | 2/2005 |
| WO | WO/01/02468 | 1/2001 |
| WO | 2005/0764080 | 8/2005 |

OTHER PUBLICATIONS

Wu, et al., A study Using Metamaterials As Antenna Substrate to Enhance Gain, Pier 51, 2005, pp. 295-328.

Mosallaei, et al, Antenna Miniaturization and Bandwidth Enhancement Using a Reactive Impedance Substrate, IEEE APS, Sep. 2004, pp. 2403-2414, vol. 52 No. 9.

Broas, et al., A High Impedance Ground Plane Applied to a Cellphone Handset Geometry, IEEE MTT, Jul. 2001, pp. 1262-1265, vol. 49 No. 7.

Lal C. Godara, Application of Antenna Arrays to Mobile Communications, Part I: Performance Improvement, Feasibility, and System Considerations, Proceedings of the IEEE, Jul. 1997, pp. 1031-1060, vol. 85, No. 7.

Lal C. Godara, Application of Antenna Arrays to Mobile Communications, Part II: Beam-Forming and Direction-of-Arrival Considerations, Proceedings of the IEEE, Aug. 1997, pp. 1195-1245, vol. 85, No. 8.

(PCTY/US2009/068157) PCT Notification of Transmittal of the International Search Report and the Written Opinion of the International Searching Authority, mailed Apr. 1, 2010. 9 pages.

* cited by examiner

PHASED ARRAY COFIRE ANTENNA STRUCTURE AND METHOD FOR OPERATING THE SAME

TECHNICAL FIELD

The present invention relates generally to implantable medical devices (IMDs) and, more particularly, the present invention relates to telemetry antennas suitable for deployment in IMDs.

BACKGROUND

Various types of devices have been developed for implantation into the human body to provide various types of health-related therapies, diagnostics and/or monitoring. Examples of such devices, generally known as implantable medical devices (IMDs), include cardiac pacemakers, cardioverter/defibrillators, cardiomyostimulators, cardiac event monitors, various physiological stimulators including nerve, muscle, and deep brain stimulators, various types of physiological monitors and sensors, and drug delivery systems, just to name a few. IMDs typically include functional components contained within a hermetically sealed enclosure or housing, which is sometimes referred to as a "can." In some IMDs, a connector header or connector block is attached to the housing, and the connector block facilitates interconnection with one or more elongated electrical medical leads. The header block is typically molded from a relatively hard, dielectric, non-conductive polymer. The header block includes a mounting surface that conforms to, and is mechanically affixed against, a mating sidewall surface of the housing.

It has become common to provide a communication link between the hermetically sealed electronic circuitry of the IMD and an external programmer, monitor, or other external medical device ("EMD") in order to provide for downlink telemetry transmission of commands from the EMD to the IMD and to allow for uplink telemetry transmission of stored information and/or sensed physiological parameters from the IMD to the EMD. Conventionally, the communication link between the IMD and the EMD is realized by encoded radio frequency ("RF") transmissions between an IMD telemetry antenna and transceiver and an EMD telemetry antenna and transceiver. Generally, the IMD antenna is disposed within the hermetically sealed housing. However, the typically conductive housing can limit the radiation efficiency of the IMD RF telemetry antenna, thereby traditionally limiting the data transfer distance between the programmer head and the IMD RF telemetry antenna to a few inches. This type of system may be referred to as a "near field" telemetry system. In order to provide for "far field" telemetry, or telemetry over distances of a few to many meters from an IMD or even greater distances, attempts have been made to provide antennas outside of the hermetically sealed housing and within the header block. Many of such attempts of positioning an RF telemetry antenna outside of the hermetically sealed housing and in the header block have utilized wire antennas or planar, serpentine antennas, such as the antennas described in U.S. Pat. No. 7,317,946, which is hereby incorporated by reference in its entirety. The volume associated with the antenna and header block conventionally required for the implementation of distance telemetry in implanted therapy and diagnostic devices has been a significant contributor to the size of the IMD.

SUMMARY

In one or more embodiments, an antenna structure for an implantable medical device (IMD) is provided that includes an antenna embedded within a structure derived from a plurality of discrete dielectric layers. A plurality of electrodes are connected to the antenna structure and arranged for applying a bias across at least a portion of at least one of the dielectric layers. The electrodes are connected to a power source in the IMD. A controller is communicatively coupled with the antenna for sending and receiving telemetry signals. In operation, the IMD is configured to measure a performance of the antenna based on certain characteristics of the signals being received by the antenna and cause a bias to be applied between the plurality of electrodes to at least a portion of a dielectric layer to alter the performance of the antenna. In one or more embodiments, an array of the plurality of electrodes may be provided such that selectable segments of dielectric material between corresponding electrodes in the array may be biased. In this manner, a phased array antenna is provided that allows a bias to be applied to alter the operating characteristics of the antenna structure. In some embodiments, the bias can be selected to provide desired impedance matching between the antenna and the surrounding environment of the implant location to mitigate energy reflection effects at the transition from the antenna structure to the surrounding environment. In some embodiments, the bias can be selected in order to provide beam steering functionality to the antenna, such that signals communicated to and from the antenna can be selectably directed in a desired direction. In some embodiments, the bias can be selected in order to provide beam steering functionality to the antenna, such that interfering signals are attenuated (i.e., that might otherwise disrupt desired communication). In some embodiments, the bias can be selected in order to alter the gain of the signals received by the antenna.

In one or more embodiments, the IMD can be configured to select the desired bias to be applied for the phased array antenna by monitoring the characteristics of the signals received by the antenna. For example, the signal strength (e.g., RSSI), error vector magnitude (e.g., EVM), or the bit error rate of the received signals can be measured to assess the performance of the antenna, where the bias selected to be applied to the dielectric material will alter the performance of the antenna (e.g., the signal strength or bit error rate) to a desired level.

In one or more embodiments, the antenna structure may be formed as a cofired monolithic structure derived from the plurality of discrete dielectric layers having an antenna conductor embedded within multiple layers of the plurality of dielectric layers. By forming a monolithic antenna structure derived from the plurality of dielectric layers, the dielectric constants of the plurality of dielectric layers can be selected and further controlled by the bias applied to control the effective dielectric between the antenna and the surrounding environment to suit the needs of the particular IMD and/or the particular implant location. In one or more embodiments, the dielectric layers comprise at least one of a low temperature co-fire ceramic (LTCC) material and/or a high temperature co-fire ceramic (HTCC) material, where the ceramic dielectric layers, the antenna, and the plurality of electrodes can be co-fired together to form a monolithic antenna structure.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

The following detailed description is merely illustrative and is not intended to limit the invention or the application and uses of the invention. Furthermore, there is no intention to be bound by any expressed or implied theory presented in the preceding technical field, background, brief summary or the following detailed description.

The following description refers to components or features being "connected" or "coupled" together. As used herein, unless expressly stated otherwise, "connected" means that one component/feature is directly or indirectly connected to another component/feature, and not necessarily mechanically. Likewise, unless expressly stated otherwise, "coupled" means that one component/feature is directly or indirectly coupled to another component/feature, and not necessarily mechanically. Thus, although the figures may depict example arrangements of elements, additional intervening elements, devices, features, or components may be present in an actual embodiment (assuming that the functionality of the IMDs are not adversely affected).

In one or more embodiments, an IMD having a phased array antenna structure derived from a plurality of discrete dielectric layers is provided. For the sake of brevity, conventional techniques and aspects related to RF antenna design, IMD telemetry, RF data transmission, signaling, IMD operation, connectors for IMD leads, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

An IMD antenna generally has two functions: to convert the electromagnetic power of a downlink telemetry transmission of an EMD telemetry antenna propagated through the atmosphere (and then through body tissues) into a signal (e.g., a UHF signal or the like) that can be processed by the IMD transceiver into commands and data that are intelligible to the IMD electronic operating system; and to convert the uplink telemetry signals (e.g., a UHF signal or the like) of the IMD transceiver electronics into electromagnetic power propagated through the body tissue and the atmosphere so that the EMD telemetry antenna or antennas can receive the signals.

Figure 1:
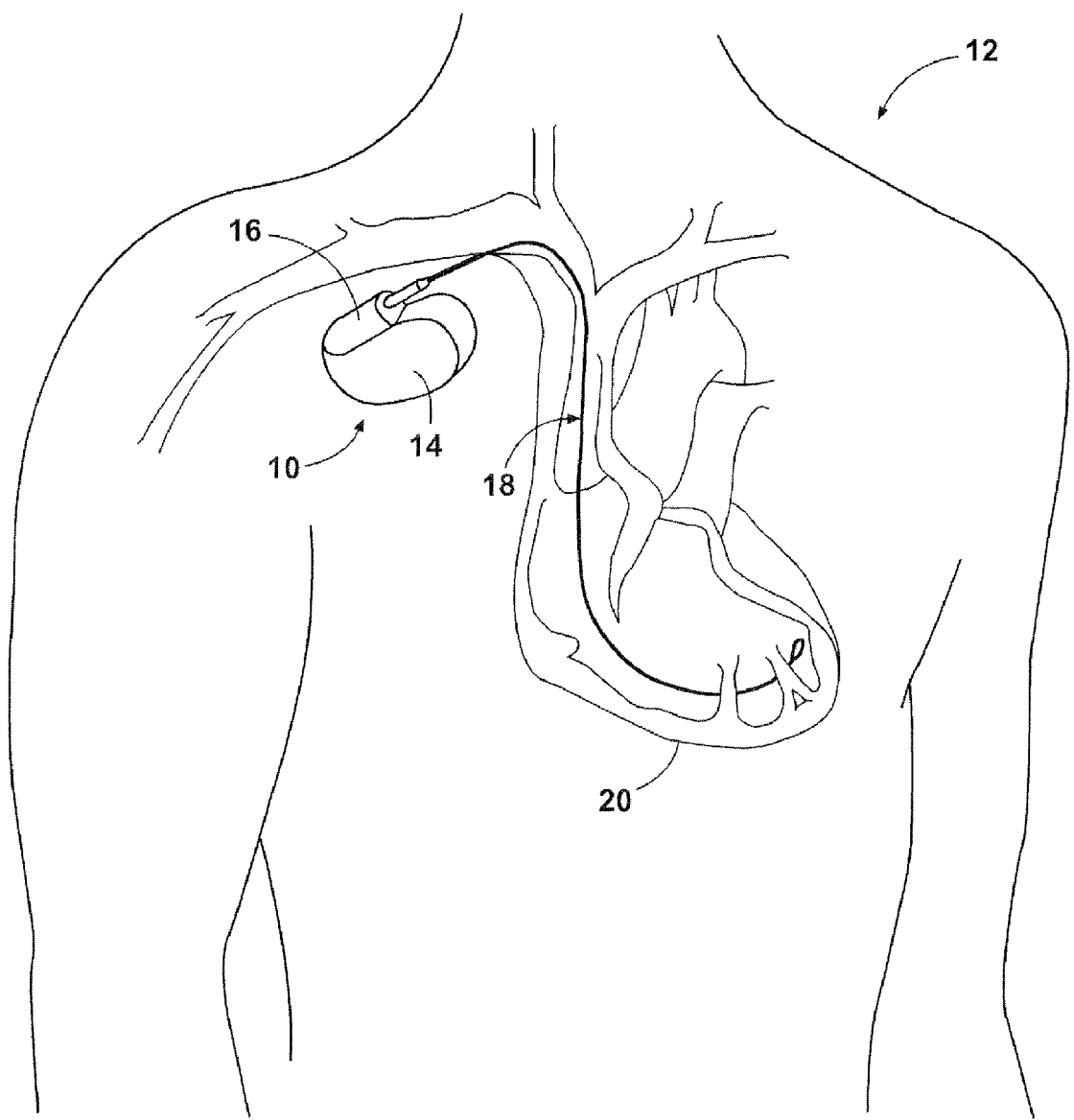
FIG. 1 illustrates an implantable medical device implanted in a human body in accordance with one or more embodiments of the present disclosure.

FIG. 1 is a perspective view of an IMD 10 implanted within a human body 12 in which one or more embodiments of the invention may be implemented. IMD 10 comprises a hermetically sealed housing 14 (or "can") and connector header or block module 16 for coupling IMD 10 to electrical leads and other physiological sensors arranged within body 12, such as pacing and sensing leads 18 connected to portions of a heart 20 for delivery of pacing pulses to a patient's heart 20 and sensing of heart 20 conditions in a manner well known in the art. For example, such leads may enter at an end of header block 16 and be physically and electrically connected to conductive receptacles, terminals, or other conductive features located within header block 16. IMD 10 may be adapted to be implanted subcutaneously in the body of a patient such that it becomes encased within body tissue and fluids, which may include epidermal layers, subcutaneous fat layers, and/or muscle layers. While IMD 10 is depicted in FIG. 1 in an ICD configuration, it is understood that this is for purposes of illustration only and IMD 10 may comprise any type of medical device requiring a telemetry antenna.

In some embodiments, hermetically sealed housing 14 is generally circular, elliptical, prismatic, or rectilinear, with substantially planar major sides joined by perimeter sidewalls. Housing 14 is typically formed from pieces of a thin-walled biocompatible metal such as titanium. Two half sections of housing 12 may be laser seam welded together using conventional techniques to form a seam extending around the perimeter sidewalls. Housing 14 and header block 16 are often manufactured as two separate assemblies that are subsequently physically and electrically coupled together. Housing 14 may contain a number of functional elements, components, and features, including (without limitation): a battery; a high voltage output capacitor; integrated circuit ("IC") devices; a processor or controller; memory elements; a therapy module or circuitry; an RF module or circuitry; and an antenna matching circuit. These components may be assembled in spacers and disposed within the interior cavity of housing 14 prior to seam welding of the housing halves. During the manufacturing process, electrical connections are established between components located within housing 14 and elements located within header block 16. For example, housing 14 and header block 16 may be suitably configured with IC connector pads, terminals, feedthrough elements, and other features for establishing electrical connections between the internal therapy module and the therapy lead connectors within header block 16 and for establishing connections between the internal RF module and a portion of a telemetry antenna located within header block 16. Structures and techniques for establishing such electrical (and physical) feedthrough connections are known to those skilled in the art and, therefore, will not be described in detail herein. For example, U.S. Pat. No. 6,414,835 describes a capacitive filtered feedthrough array for an implantable medical device, the contents of which are hereby incorporated by reference.

Header block 16 is preferably formed from a suitable dielectric material, such as a biocompatible synthetic polymer. In some embodiments, the dielectric material of header block 16 may be selected to enable the passage of RF energy that is either radiated or received by a telemetry antenna (not shown in FIG. 1) encapsulated within header block 16. The specific material for header block 16 may be chosen in response to the intended application of IMD 10, the electrical characteristics of the environment surrounding the implant location, the desired operating frequency range, the desired RF antenna range, and other practical considerations.

Figure 2:
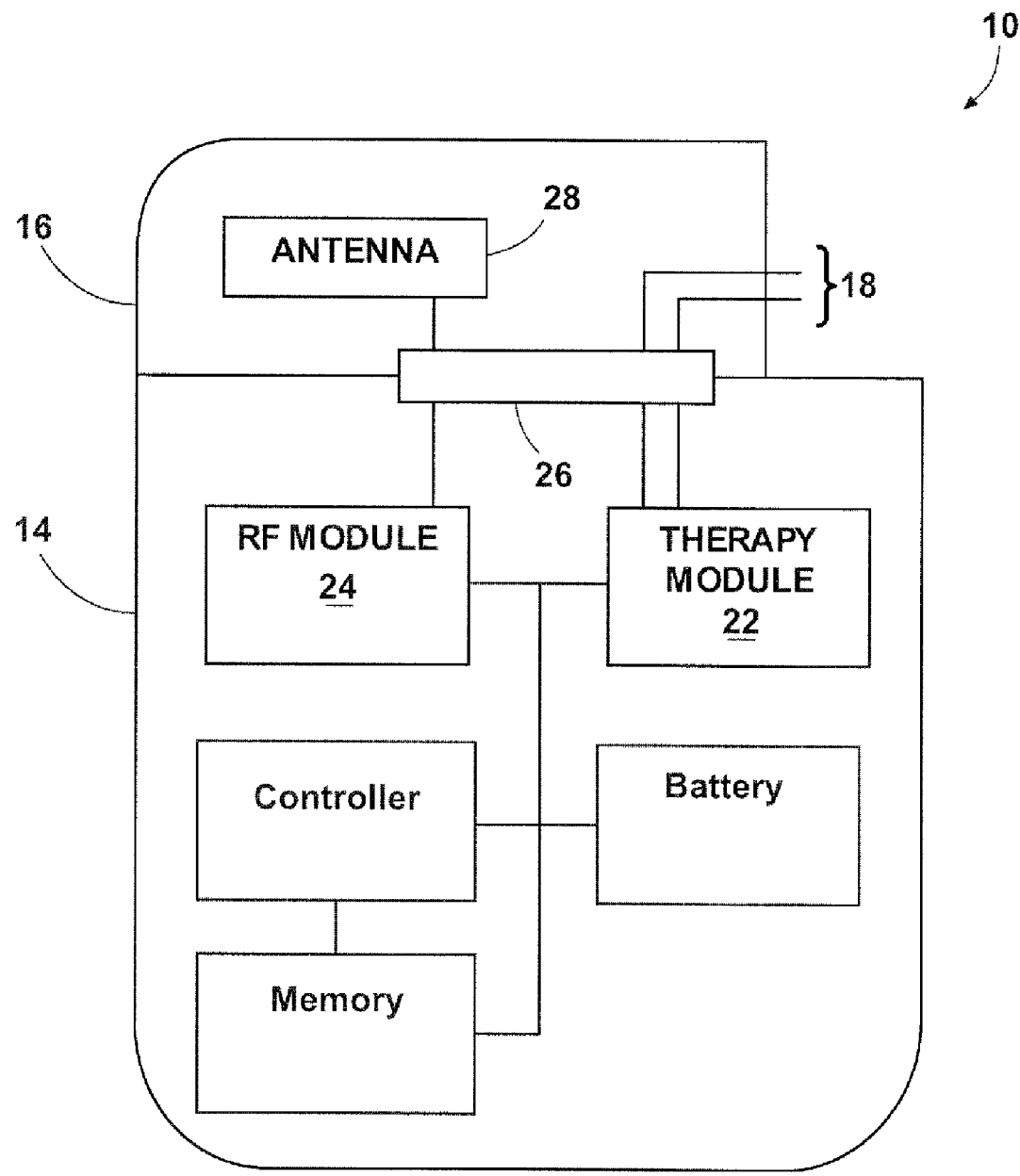
FIG. 2 is a schematic block diagram illustration of exemplary implantable medical device in accordance with one or more embodiments of the present disclosure.

FIG. 2 is a simplified schematic representation of an IMD 10 and several functional elements associated therewith. IMD 10 generally includes hermetically sealed housing 14 and header block 16 coupled to housing 14, a therapy module 22 contained within housing 14, and an RF module 24 contained within housing 14. In practice, IMD 10 will also include a number of conventional components and features necessary to support the functionality of IMD 10 as known in the art, such as a controller, a memory and battery as a power source. Such conventional elements may not be fully described herein.

Therapy module 22 may include any number of components, including, without limitation: electrical devices, ICs, microprocessors, controllers, memories, power supplies, and the like. Briefly, therapy module 22 is configured to provide the desired functionality associated with the IMD 10, e.g., defibrillation pulses, pacing stimulation, patient monitoring, or the like. In this regard, therapy module 22 may be coupled to one or more sensing or therapy leads 18. In practice, the connection ends of therapy leads 18 are inserted into header block 16, where they establish electrical contact with conductive elements coupled to therapy module 22. Therapy leads 18 may be inserted into suitably configured lead bores formed within header block 16. In the example embodiment, IMD 10 includes a feedthrough element 26 that bridges the transition between housing 14 and header block 16. Therapy leads 18 extend from header block 16 for routing and placement within the patient.

RF module 24 may be positioned inside or outside of housing 14 and may include any number of components, including, without limitation: electrical devices, ICs, amplifiers, signal generators, a receiver and a transmitter (or a transceiver), modulators, microprocessors, controllers, memories, power supplies, and the like. RF module 24 may further include a matching circuit or a matching circuit may be positioned between RF module 24 and antenna 28. Matching circuit may include any number of components, including, without limitation: electrical components such as capacitors, resistors, or inductors; filters; baluns; tuning elements; varactors; limiter diodes; or the like, that are all suitably configured to provide impedance matching between antenna 28 and RF module 24, thus improving the efficiency of antenna 28. Briefly, RF module 24 supports RF telemetry communication for IMD 10, including, without limitation: generating RF transmit energy; providing RF transmit signals to antenna 28; processing RF telemetry signals received by antenna 28, and the like. In practice, RF module 24 may be designed to leverage the conductive material used for housing 14 as an RF ground plane (for some applications), and RF module 24 may be designed in accordance with the intended application of IMD 10, the electrical characteristics of the environment surrounding the implant location, the desired operating frequency range, the desired RF antenna range, and other practical considerations.

Antenna 28 is coupled to RF module 24 to facilitate RF telemetry between IMD 10 and an EMD (not shown). Generally, antenna 28 is suitably configured for RF operation (e.g., UHF or VHF operation, 401 to 406 MHz for the MICS/MEDS bands, 900 MHz/2.4 GHz and other ISM bands, etc.). In the example embodiment shown in FIG. 2, antenna 28 is located within header block 16 and outside of housing 14. However, the volume associated with the antenna 28 and the volume within the header block 16 required for the implementation of distance telemetry in implanted therapy and diagnostic devices can be a significant contributor to the size of the IMD 10. Antenna 28 may have characteristics resembling a monopole antenna, characteristics resembling a dipole antenna, characteristics resembling a coplanar waveguide antenna, characteristics resembling a stripline antenna, characteristics resembling a microstrip antenna, and/or characteristics resembling a transmission line antenna. Antenna 28 may also have any number of radiating elements, which may be driven by any number of distinct RF signal sources. In this regard, antenna 28 may have a plurality of radiating elements configured to provide spatial, pattern or polarization diversity In one or more embodiments, antenna 28 is coupled to RF module 24 via an RF feedthrough in feedthrough 26, which bridges housing 14 and header block 16. Antenna 28 may include a connection end that is coupled to RF feedthrough in feedthrough 26 via a conductive terminal or feature located within header block 16. Briefly, a practical feedthrough 26 includes a ferrule supporting a non-conductive glass or ceramic insulator. The insulator supports and electrically isolates a feedthrough pin from the ferrule. During assembly of housing 14, the ferrule is welded to a suitably sized hole or opening formed in housing 14. RF module 24 is then electrically connected to the inner end of the feedthrough pin. The connection to the inner end of the feedthrough pin can be made by welding the inner end to a substrate pad, or by clipping the inner end to a cable or flex wire connector that extends to a substrate pad or connector. The outer end of the feedthrough pin serves as a connection point for antenna 28, or as a connection point for an internal connection socket, terminal, or feature that receives the connection end of antenna 28. The feedthrough 26 for antenna 28 may be located on any desired portion of housing 14 suitable for a particular design.

Figure 3:
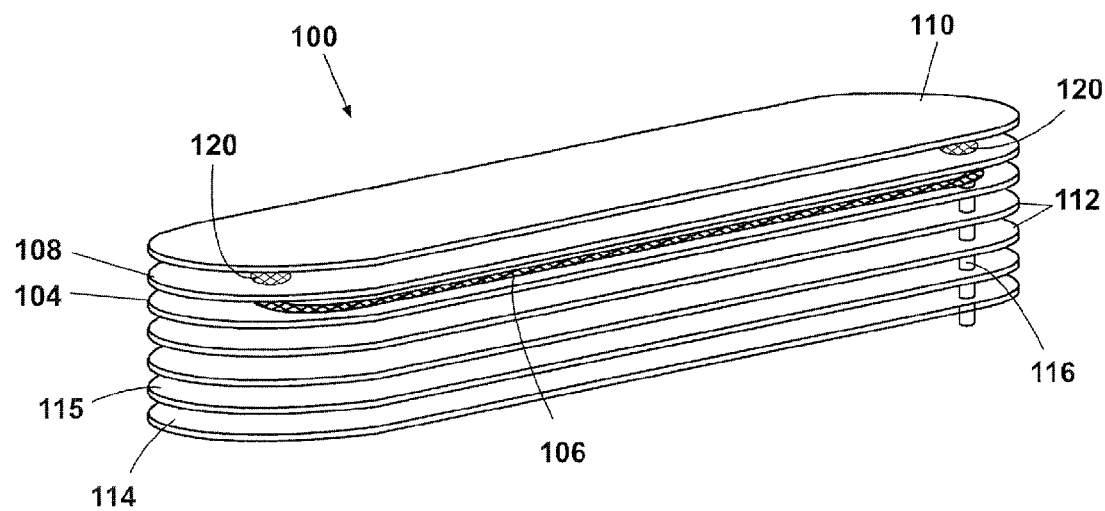
FIG. 3 is a perspective, exploded view of an antenna structure for an implantable medical device formed in accordance with one or more embodiments of the present disclosure.

Referring now to FIG. 3, a perspective, exploded view of an antenna structure 100 formed in accordance with one or more embodiments is respectively illustrated. Certain features and aspects of antenna structure 100 are similar to those described above in connection with antenna 28, and shared features and aspects will not be redundantly described in the context of antenna structure 100. Antenna structure 100 includes at least one antenna 106 formed on a dielectric layer 104. One or more additional discrete dielectric layers may be positioned above the antenna 106 serving as superstrates 108 and/or below the antenna 106 serving as substrates 112. In one or more embodiments, the antenna structure 100 includes a biocompatible layer 110 positioned as the outermost layer over the superstrate dielectric layers 108 serving as an interface between the antenna structure 110 and the surrounding environment. In some embodiments, the biocompatible layer 110 may comprise the outermost of the superstrate dielectric layers 108. Different types of biocompatible materials can be selected based on the intended use of antenna structure 100 and IMD 10 and the intended surrounding environment. For example, outermost layer 110 may comprise inorganic materials, such as Alumina ($Al_2O_3$), zirconium oxide ($ZrO_2$), mixtures thereof or bone-like systems [hydroxyapatite—$Ca_5$(POH)(PO_4)_3$], organic materials, such as silicone and its derivatives, and other traditionally implantable biocompatible materials.

Figure 4:
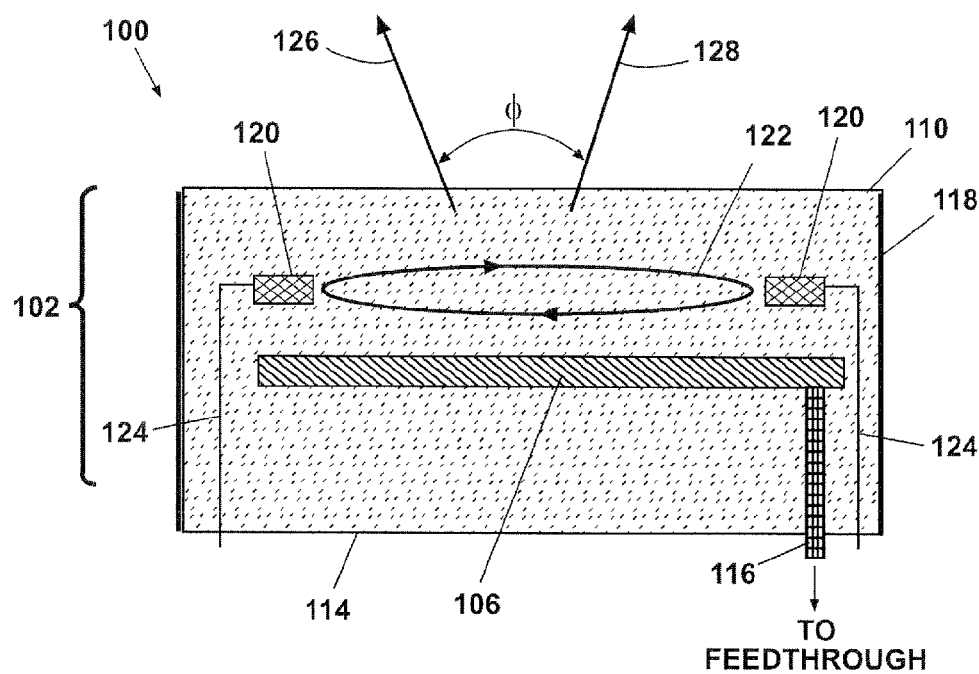
FIG. 4 is a cross-sectional side view of an antenna structure for an implantable medical device formed in accordance with one or more embodiments of the present disclosure.

With further reference to FIG. 4, in one or more embodiments, a plurality of electrodes 120 are connected to respective portions of antenna structure 100 and arranged such that a voltage bias can be applied between the electrodes 120 across at least a portion of one or more of the dielectric layers 104, 108 or 112 (with electrodes 120 being illustrated as being connected to dielectric layer 108 in FIG. 3). Electrodes are connected to a power source in IMD 10 for providing such voltage bias. A controller, either located in RF module 24 or otherwise located within IMD 10, is communicatively coupled with antenna 106 for sending and receiving telemetry signals.

In some embodiments, antenna structure 100 may include an shielding layer 114 positioned in a layer under the antenna 106 formed from a metalized material that provides electromagnetic shielding of device circuitry inside of the hermetically sealed housing 14 to which the antenna structure 100 is attached through a feedthrough via 116. In some embodiments, the shielding layer 114 is positioned as the innermost layer of the antenna structure 100, while it is understood that shielding layer 114 can also be positioned within another intermediate substrate layer 112 positioned under the antenna 106. In one or more embodiments, a layer of electromagnetic bandgap material 115 may be positioned under antenna 106 to function as an electromagnetic bandgap between antenna 106 and shielding layer 114 (i.e., ground plane). Typically, when a radiating antenna element is placed above and in parallel with a ground plane, the field radiated by the antenna element and the field reflected by the ground plane are 180° out of phase due to the reflection coefficient presented by the ground plane short circuit. As a result, when the separation distance between the antenna element and the ground plane is reduced, the total antenna radiated fields tend to zero as the field radiated from the antenna element and its ground plane reflection will tend to completely cancel each other. An electromagnetic bandgap layer 115 prevents this reduction in antenna radiation efficiency by introducing a ground perturbation known as an electromagnetic bandgap, or high impedance surface, between antenna 106 and ground plane shielding layer 114. The electromagnetic bandgap layer 115 prevents or minimizes a reduction in antenna radiation efficiency from occurring as a result of the close proximity of the antenna conductor 106 to the ground plane 114. In one aspect, the electromagnetic bandgap layer 115 at resonance appears as an open circuit with a reflection coefficient in phase with the incident field. For instance, the electromagnetic bandgap layer 115 will cause the field radiated from antenna 106 and the field radiated by its ground plane image to be co-directed thus maintaining the same orientation and not canceling each other out. The electromagnetic bandgap layer 115 further provides a high electromagnetic surface impedance that allows the antenna 106 to lie directly adjacent to the ground plane 114 without being shorted out. This allows compact antenna designs where radiating elements are confined to limited spaces Thus, the electromagnetic bandgap layer 115 assists in miniaturization of the device by allowing the distance between antenna 106 and ground plane shielding layer 114 to be reduced to a small distance. In one or more embodiments, electromagnetic bandgap layer 115 may be vacuum deposited on the surface of one of the layers of the device 100 or adhered via epoxy after ceramic densification (described later) in order to minimize material alterations induced by thermal excursion of the firing process.

In one or more embodiments, dielectric layers 104, 108 and 112 can be selected to possess respective dielectric constants that match the dielectric constant of the environment (e.g., body tissue) surrounding the antenna structure 100 to mitigate energy reflection effects at the transition from the antenna structure 100 to the surrounding environment. This matching of dielectric constants in the various layers of device 100 can be achieved by incorporating materials that are cofireable, compatible and possess desired dielectric constants.

In one or more embodiments, various biocompatible layers formed for the superstrate dielectric layers 108 may comprise polymers that are loaded with high dielectric constant powders, such that powders with different dielectric constants can be loaded on the different polymer layers, different concentrations of powder loading can be performed on the different polymer layers, or the dielectric constant of each polymer layer can otherwise have its powder loading adjusted to produce a structure having a desired effective dielectric constant for the superstrate dielectric layers 108. In one or more embodiments, the substrate dielectric layers 112 under conductor 106 may comprise materials with higher dielectric values than dielectric layer 104 on which antenna 106 is formed, such that the higher dielectric values associated with substrate dielectric layers 112 allow the distance between antenna conductor 106 and ground plane shielding layer 114 to be minimized, thereby allowing a reduction in size of antenna structure 100 to be achieved. The high dielectric constant K of each layer may be achieved by incorporating cofireable materials having high dielectric constants K (e.g., capacitive materials). Depending upon the materials used to form substrate dielectric layers 112, dielectric constant values can vary anywhere from k=5-6 for the LTCC layer itself to at least 1-2 orders of magnitude higher with the use of capacitive pastes that are LTCC compatible. In addition, a ceramic loaded printed wiring board (PWB) is another embodiment to the LTCC based structure. LTCC materials offer the ability to embed passive components to spatially and functionally tailor the dielectric constant or capacitance to optimize packaging efficiency and/or performance. Since materials with high dielectric constants are typically not biocompatible, substrate dielectric layers 112 may be separated and isolated from potential contact with body environment surrounding IMD 10 by the biocompatible materials used to form outermost biocompatible layer 110 or other superstrate dielectric layers 108. The isolation of substrate layers 112 from the body environment surrounding IMD 10 allows the possible selection of materials for superstrate dielectric layers 108 to be wide ranging. For example, dielectric oxide (e.g., barium titanium oxide ($BaTiO_3$)) based systems with dielectric constants k in the hundreds to thousands are possible.

In one or more embodiments, the various layers used to form antenna structure 100 may be formed using any material layer deposition technique known in the art, including but not limited to depositing, spraying, screening, dipping, plating, etc. In some embodiments, molecular beam epitaxy (MBE), atomic layer deposition (ALD) or other thin film, vacuum deposited processes may be used to deposit the various layers building them on top of one another, such that ALD allows thin high dielectric materials to be used in forming substrate dielectric layers 112 and thin lower dielectric materials to be used in forming superstrate dielectric layers 108, thereby achieving size reduction and miniaturization of overall antenna structure 100 while still improving performing of antenna structure 100. The metal layers can be stacked to form a stacked plate capacitor structure to increase the dielectric constant of the area surrounding the antenna 106.

In one or more embodiments, after the various layers of antenna structure 100 and formed or otherwise deposited with respect to one another, as illustrated in FIG. 3, the various layers may be co-fired to a monolithic structure 102 derived from the various layers, as illustrated in FIG. 4, having antenna 106 embedded within the resulting monolithic structure 102. Feedthrough via 116 extends through monolithic structure 102 and may be used to connect antenna 106 to housing 14, such as through a feedthrough. By forming a monolithic antenna structure 102 derived from the plurality of dielectric layers 104, 108 and 112, the dielectric constants of the plurality of dielectric layers 104, 108 and 112 can be selected or controlled to provide matching characteristics and the dimensions of the overall antenna structure can be minimized to provide a miniature antenna structure.

In one or more embodiments, the material properties of at least a portion of at least one of the plurality of dielectric layers 104, 108 and 112 can further be altered or adjusted by subjecting such portion of dielectric layers 104, 108 and 112 to an electric field. The electric field 122 is initiated in the selected portion of dielectric layers 104, 108 and 112 by applying a voltage bias between corresponding electrodes 120. Electrical connections 124 (e.g., traces of biocompatible conductive material) connect electrodes 120 to a power source (not shown in FIG. 4) in IMD 10. For example, the dielectric constant and/or capacitance of at least a portion of at least one of dielectric layers 104, 108 and 112 (or the resulting dielectric material in the cofired structure 102) can be altered or changed by appropriately applying a desired voltage bias between electrodes 120. By altering the material properties of the selected portion of the dielectric material with the applied bias, the overall performance characteristics of antenna 106 can be selectively controlled.

In one or more embodiments, the biasing of electrodes 120 can be selected to alter the effective dielectric constant of the dielectric material surrounding antenna 106 in order to provide a desired impedance matching between antenna 106 and the surrounding environment of the implant location to mitigate energy reflection effects at the transition from antenna structure 102 to the surrounding environment. In one or more embodiments, the biasing of electrodes 120 can be selected to alter the gain of the signals received by antenna 106. Depending upon the implant location of IMD 10 and the particular surrounding environment of the implant location (e.g., tissue or body mass having different dielectric values or depth of implant location, etc.), the operating characteristics of antenna 106 will be affected by such conditions of the surrounding environments. The biasing of electrodes 120 allows the operating performance characteristics of antenna 106 to be adjusted to account for such conditions of the surrounding environments, such as by adjusting the bias to alter the impedance matching between antenna 106 and the surrounding environment or to alter the gain of antenna 106. This allows the operation of telemetry communications to be fine tuned for optimal antenna performance after IMD 10 has been implanted within a patient 12.

In one or more embodiments, the biasing of electrodes 120 can be selected to beam steering functionality to antenna 106, such that signals communicated to and from antenna 106 can be selectably directed in a desired direction. Referring to FIG. 4, antenna 106 may have a radiation emission direction 126 under unbiased conditions, where segments of antenna structure 102 can be biased to introduce a phase shift ($\phi$) to modify the wave propagation characteristics of communicating signals through application of an electric field 122 to a segment of antenna structure 102. Thus, the introduced phase shift ($\phi$) could alter the radiation emission direction to direction 128. In this manner, the biasing of electrodes 120 can be selected to provide beam steering functionality to antenna 106 by introducing a introduced phase shift ($\phi$). Such beam steering functionality can be used to improve the quality of telemetry transmissions. Further, when multiple external devices are capable of communicating with IMD 10 or when multiple IMDs are present at a certain location capable of communicating with one particular external device, such beam steering functionality can be utilized to control the direction of communications to ensure communication only occurs between two intended devices (i.e., Space Division Multiple Access (SDMA)). In some embodiments, the biasing of electrodes 120 can be selected in order to provide beam steering functionality to antenna 106, such that the phase shift ($\phi$) and resultant antenna directivity attenuates undesired (i.e., interfering) signals that might otherwise degrade desired communications.

Figure 5:
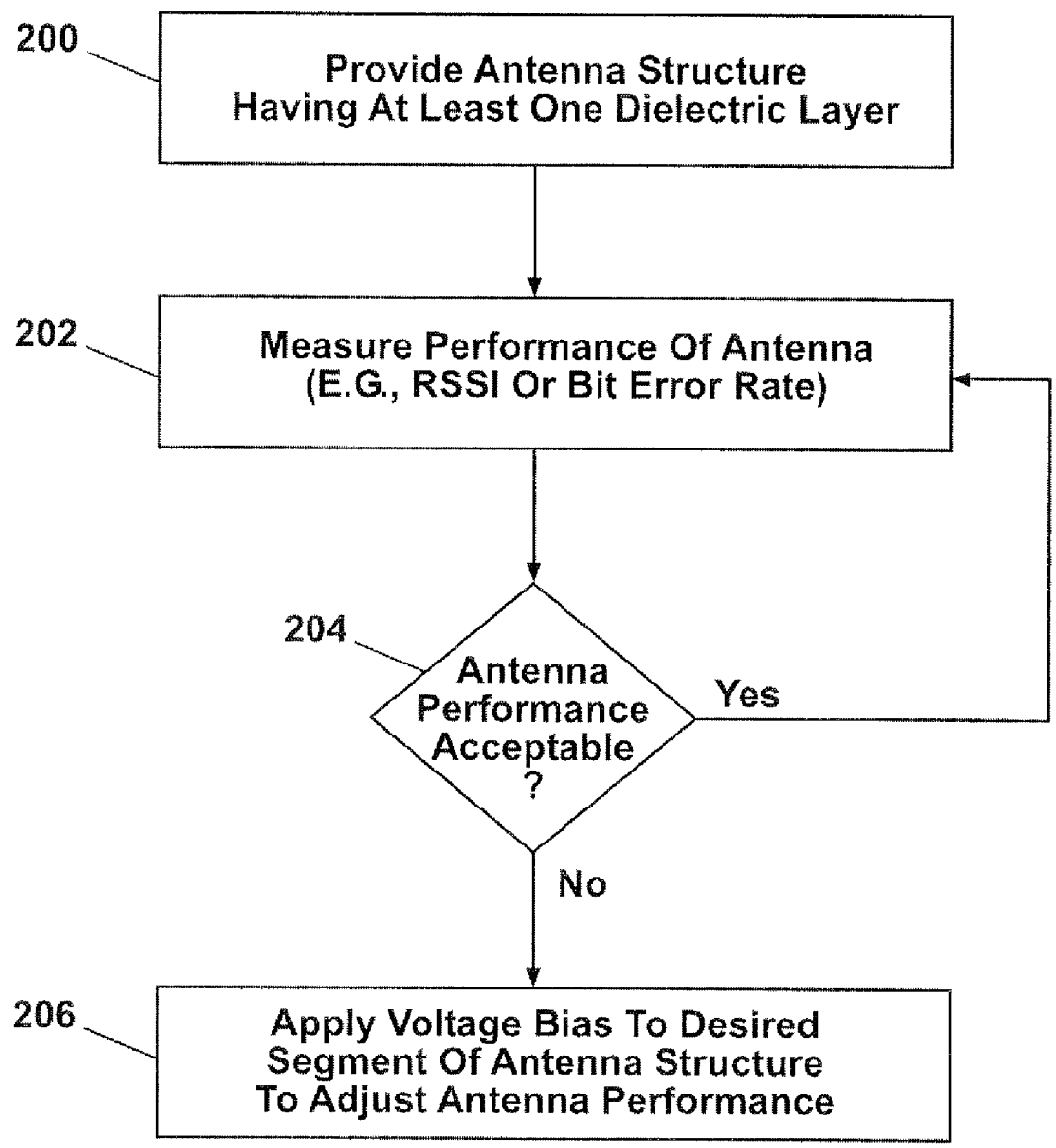
FIG. 5 is an operational flow diagram of a method for applying a bias to adjust performance of the antenna structure of the implantable medical device in accordance with one or more embodiments of the present disclosure.

In operation, referring to the operational flow diagram of FIG. 5, IMD 10 is configured to operate an algorithm stored in its memory to control the operating characteristics of antenna structure 102. Initially, an antenna structure 102 as described herein is provided (operation 200) having an antenna structure 102 comprising antenna 106 embedded within at least one layer of dielectric material. In operation 202, a performance of antenna 106 is measured based on certain monitored characteristics of the signals being received by antenna 106, and it is determined in operation 204 whether the performance of antenna 106 is acceptable. For example, the signal strength (e.g., RSSI), error vector magnitude (e.g., EVM), or the bit error rate of the received signals can be measured to assess the performance of antenna 106. If antenna 106 is operating as desired, then no adjustments to the operation of the overall antenna structure may be required and IMD 10 may either do nothing or may continue to monitor the characteristics of the signals being received by antenna 106. If antenna 106 is not operating as desired, then IMD 10 will cause a bias to be applied in operation 206 to at least a portion of antenna structure 102 (i.e., a portion of at least one dielectric layer 104, 108, or 112) between electrodes to alter the material properties of the dielectric material and thus alter the performance of antenna 106. In this manner, a bias can be used on a segment of antenna structure 102 to control the operating characteristics of the antenna structure 102. The embodiment described is merely illustrative as the analytical algorithms for generating said bias are well known in the art and any of such analytical algorithms could be utilized, such as those described in the paper, "Applications of Antenna Arrays to Mobile Communications, Part II: Beam-Forming and Direction-of-Arrival Considerations," by Lal C. Godara, Proceedings of the IEEE, Vol. 85, No. 8, August 1997, the contents of which are hereby incorporated by reference in its entirety.

Figure 6:
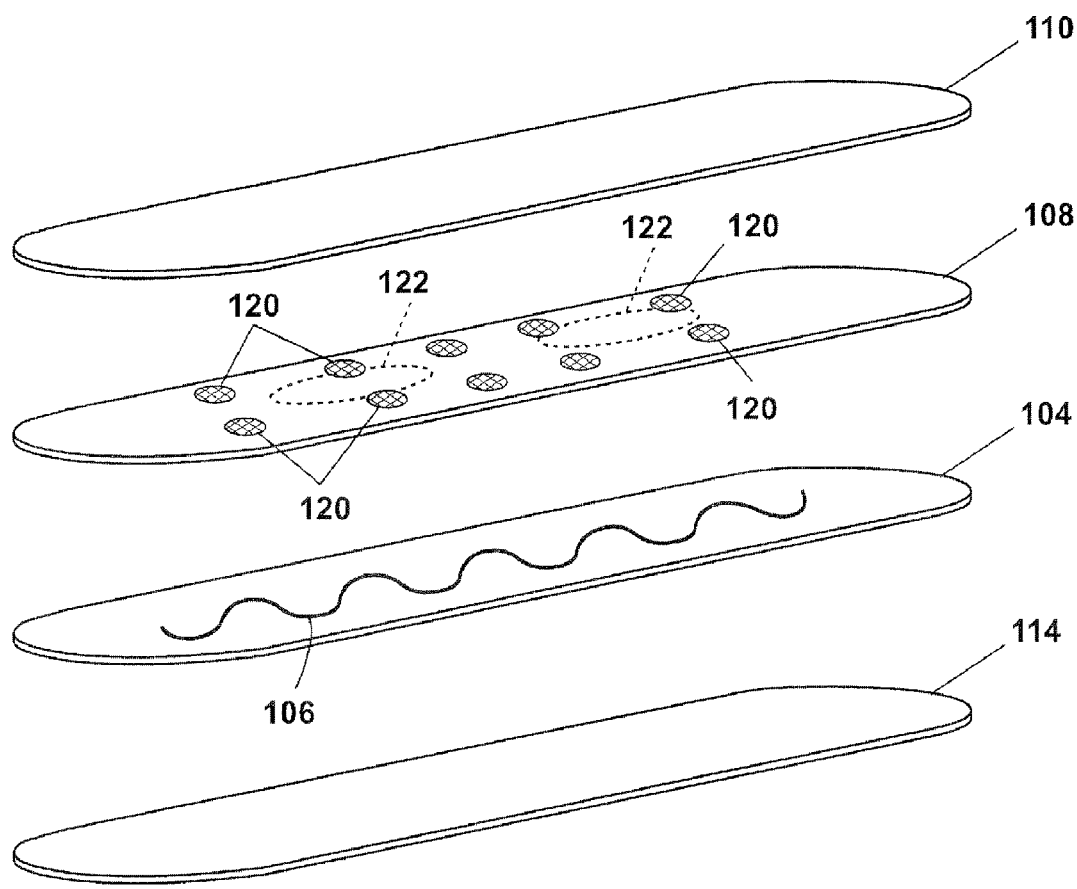
FIG. 6 is a perspective, exploded view of an antenna structure having an array of electrodes formed on a superstrate dielectric layer in accordance with one or more embodiments of the present disclosure.

In one or more embodiments, the plurality of electrodes 120 are formed as an array of electrodes 120 that are arranged to impart an electric field 122 on selected segments of superstrate dielectric layer 108, as illustrated in FIG. 6. A voltage bias may be variably selected to be generated between particular combinations of electrodes 120 to bias particular segments of dielectric layer 108 in order to alter the operating characteristics of the antenna structure 102 in different manners. Electrodes 120 may be formed to be positioned on dielectric layer 108, to extend at least partially through dielectric layer 108, to be positioned on a side surface of dielectric layer 108, or any combination thereof, in order to create different possible segments of dielectric layer 108 capable of being biased. In this manner, the material properties of selected segments of superstrate dielectric layer 108 can be adjusted by the selected biasing in the path of the emitted radiation from antenna 106.

Figure 7:
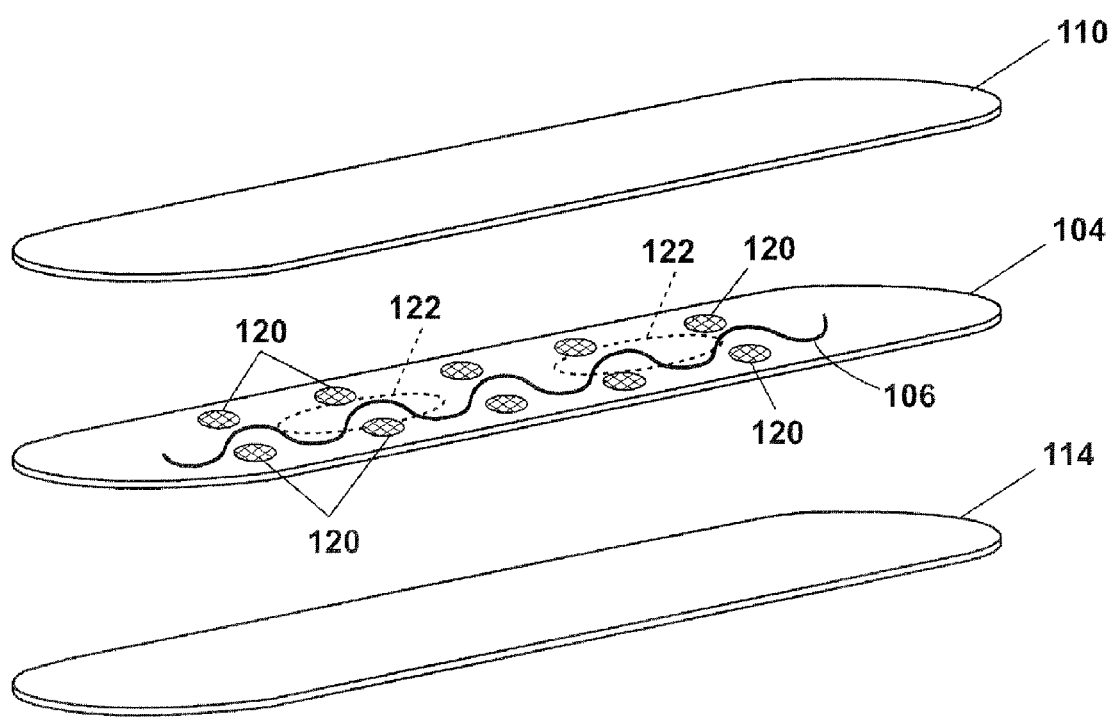
FIG. 7 is a perspective, exploded view of an antenna structure having an array of electrodes formed on the same dielectric layer as the antenna in accordance with one or more embodiments of the present disclosure.
Figure 8:
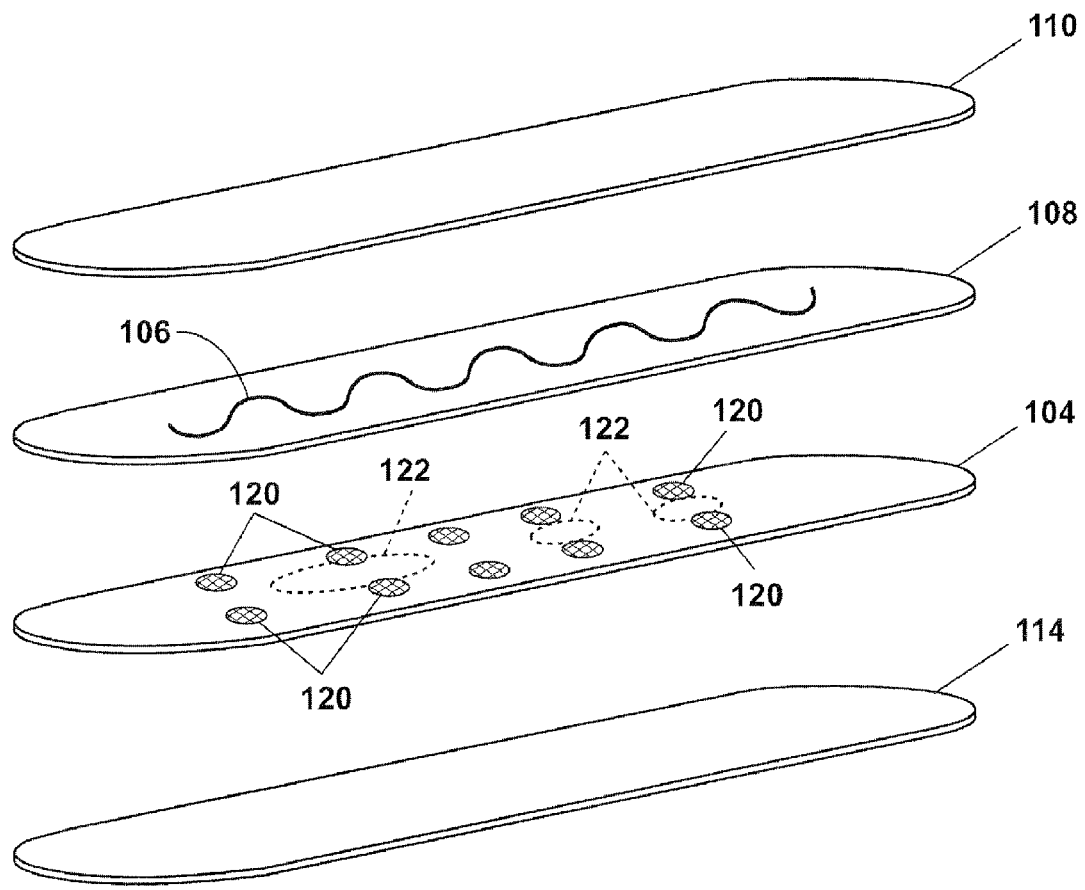
FIG. 8 is a perspective, exploded view of an antenna structure having an array of electrodes formed on a substrate dielectric layer in accordance with one or more embodiments of the present disclosure.

In one or more embodiments, the array of electrodes 120 may be formed on the same dielectric layer 104 as antenna 106 is formed on, as illustrated in FIG. 7. In one or more embodiments, the array of electrodes 120 may be formed on a substrate dielectric layer 112 formed under antenna 106, as illustrated in FIG. 8.

Figure 9:
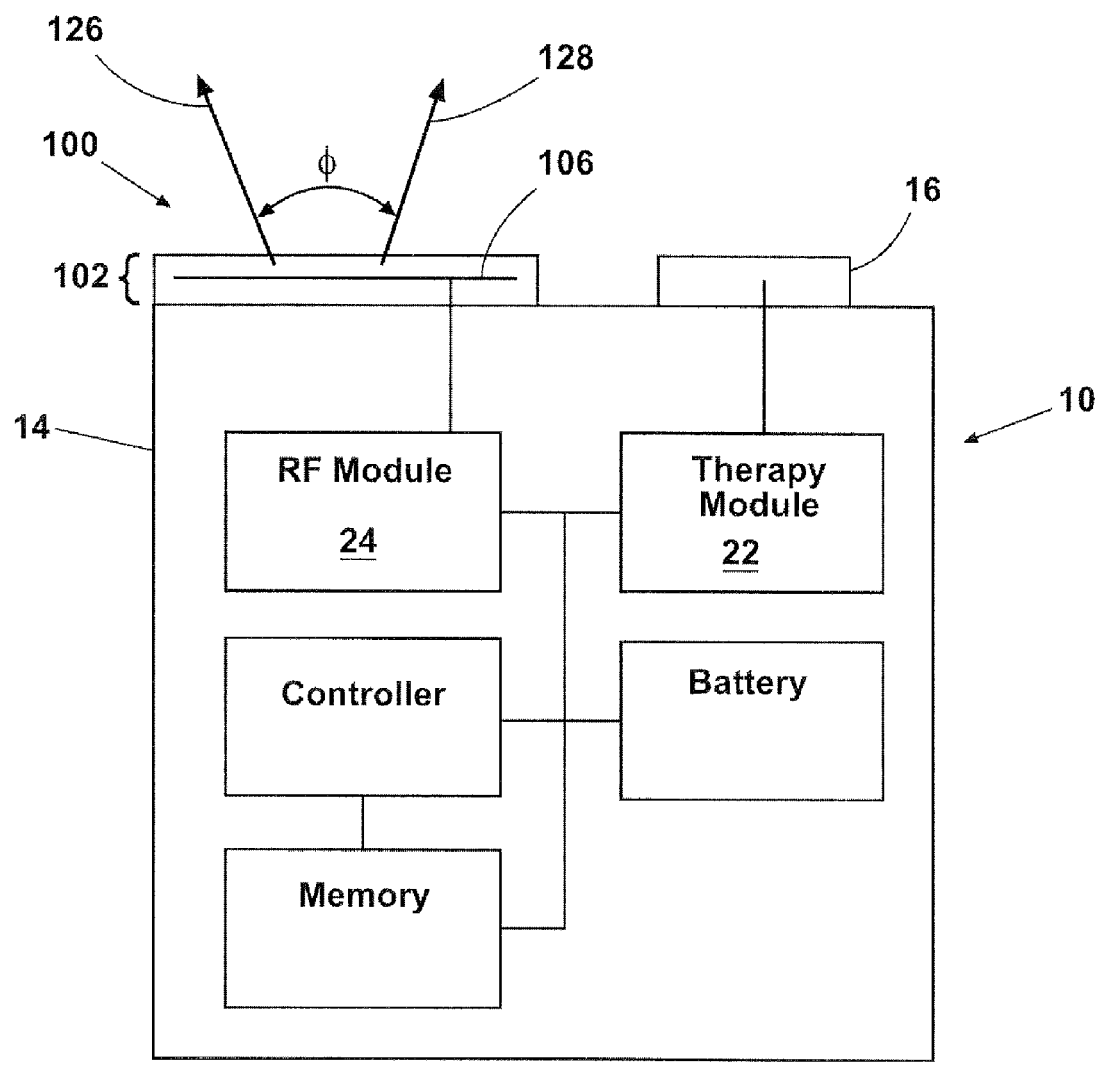
FIG. 9 is a schematic block diagram illustration of another exemplary implantable medical device in accordance with one or more embodiments of the present disclosure.

In one or more embodiments, after the antenna structure 100 has been formed as a co-fired monolithic structure 102, the edges 118 or side surfaces of the various layers of the antenna structure 100 (i.e., dielectric layers 104, 108 and 112, electromagnetic bandgap layer 115, outermost biocompatible layer 110 and innermost shielding layer 114) may be brazed or otherwise sealed to hermetically seal the edges 118 of antenna structure 100. The brazed side edges 118 along with the outermost biocompatible layer 110 of antenna structure 100 provide a hermetic seal for antenna structure 100 so that it can be connected directly to housing 14 without requiring a header to enclose and seal the antenna conductor 106, as typically required with conventional far field telemetry antennas for IMDs. As illustrated in FIG. 9, antenna structure 100 may be coupled to housing 14 using brazing, glassing, diffusion bonding or other suitable bonding techniques that will provide a hermetic seal, as known to those skilled in the art. The antenna structure 100 thus reduces the overall volume and physical dimension required for antenna conductor 106 for adequate radiation. In some embodiments, a header block 16 having reduced dimensions may still be utilized for connecting external leads to therapy module 16.

In one or more embodiments, antenna 106 is formed from a biocompatible conductive material, such as but not limited to at least one of the following materials: Platinum, Iridium, Platinum-Iridium alloys, Alumina, Silver, Gold, Palladium, Silver-Palladium or mixtures thereof, or Niobium, Molybdenum and/or Moly-manganese or other suitable materials. In one or more embodiments, dielectric layers 104, 108 and 112 may be comprise at least one of a ceramic material, a semiconductor material, and/or a thin film dielectric material. In some embodiments in which the dielectric layers 104 include at least one ceramic material, the dielectric layers 104, 108 and 112 may include at least one of a low temperature co-fired ceramic (LTCC) material or a high temperature co-fired ceramic (HTCC) material or a PWB material that enable the incorporation of materials having desired dielectric constant values. Generally, a LTCC material has a melting point between about 850 C.° and 1150 C.°, while a HTCC material has a melting point between about 1100 C.° and 1700 C.°. The ceramic dielectric layers 104, 108 and 112, antenna 106, electromagnetic bandgap layer 115, outermost biocompatible layer 110 and innermost shielding layer 114, via 116, electrodes 120, and the conductive pathways serving as electrical connections 124 can be sintered or co-fired together to form the monolithic antenna structure 102 including an embedded antenna conductor 106, as illustrated in FIG. 4. Methods for co-firing layers of ceramic materials together to form monolithic structures for use in IMDs are described, for example, in U.S. Pat. Nos. 6,414,835 and 7,164,572, the contents of both of which are hereby incorporated by reference in their entireties.

According to one or more embodiments, the use of a co-firing technique to form a monolithic antenna structure 102 including an embedded antenna 106 allows for the manufacture of low-cost, miniaturized, hermetically sealed antenna structures 100 suitable for implantation within tissue and/or in direct or indirect contact with diverse body fluids.

In one or more embodiments, the plurality of different individual discrete layers or sheets of materials (or segments of tape) that comprise the various ceramic dielectric layers 104, 108 and 112, antenna 106, electrodes 120, electrical connections 124, electromagnetic bandgap layer 115, outermost biocompatible layer 110 and innermost shielding layer 114 may be printed with a metalized paste and other circuit patterns, stacked on each other, laminated together and subjected to a predetermined temperature and pressure regimen, and then fired at an elevated temperature(s) during which the majority of binder material(s) (present in the ceramic) and solvent(s) (present in the metalized paste) vaporizes and/or is incinerated while the remaining material fuses or sinters. The number of dielectric layers 104, 108 and 112 may be variably selected based on the desired antenna characteristics. In some embodiments, the materials suitable for use as cofireable conductors for forming the antenna 106 are the biocompatible metal materials described herein or other materials suitable for the metalized paste. In one or more embodiments, the stacked laminates are then co-fired together at temperatures between about 850 C.° and 1150 C.° for LTCC materials and between about 1100 C.° and 1700 C.° for HTCC materials.

In one or more embodiments, the dielectric layers 104, 108 and 112 include a plurality of planar ceramic layers. Each ceramic layer may be shaped in a green state to have a desired layer thickness. In general, the formation of planar ceramic layers starts with a ceramic slurry formed by mixing a ceramic particulate, a thermoplastic polymer and solvents. This slurry is spread into ceramic sheets of predetermined thickness, from which the solvents are volitized, leaving self-supporting flexible green sheets. Holes in certain dielectric layers 104 and 112 that will be filled with conductive material to form via 116 or electrical connections 124 are made, using any conventional technique, such as drilling, punching, laser cutting, etc., through the green sheets from which the ceramic layers 104 and 112 are formed. The materials suitable for use as cofireable ceramics include alumina ($Al_2O_3$), aluminum nitride, beryllium oxide, Silica ($SiO_2$), Zirconia ($ZrO_2$), glass-ceramic materials, glass suspended in an organic (polymer) binder, or mixtures thereof.

Many of the algorithms or methods described herein may be implemented by a controller that operates programs or routines stored in memory of IMD 10. The controller may comprise any of a wide variety of hardware or software configurations capable of executing algorithms. Example hardware implementations of controller include implementations within an application specific integrated circuit (ASIC), a field programmable gate array (FPGA), a programmable logic device, specifically designed hardware components, one or more processors, or any combination thereof. If implemented in software, a computer readable medium, such as a memory in the IMD 10, may store computer readable instructions, e.g., program code, that can be executed by the controller to carry out one of more of the techniques described herein. For example, the memory may comprise random access memory (RAM), read-only memory (ROM), non-volatile random access memory (NVRAM), electrically erasable programmable read-only memory (EEPROM), flash memory, or the like.

While the system and method have been described in terms of what are presently considered to be specific embodiments, the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A method of operating an implantable medical device ("IMD"), comprising:

providing an IMD including an antenna structure having an antenna and at least one dielectric layer;

measuring a performance of the antenna based on certain characteristics of signals being received by the antenna;

applying a bias to at least a portion of the at least one dielectric layer to alter the performance of the antenna.

2. The method of claim 1, further comprising applying the bias to the at least one dielectric layer in order to provide beam steering functionality to the antenna, such that signals communicated to and from the antenna can be selectably amplified.

3. The method of claim 1, further comprising applying the bias to the at least one dielectric layer in order to provide beam steering functionality to the antenna, such that signals communicated to and from the antenna can be selectably attenuated.

4. The method of claim 1, further comprising applying the bias to the at least one dielectric layer in order to alter the gain of the signals received by the antenna.

5. The method of claim 1, further comprising applying the bias to the at least one dielectric layer in order to achieve impedance matching between the antenna and a propagation environment surrounding an implant location for the IMD.

6. The method of claim 1, further comprising:

measuring at least one of a signal strength, error vector magnitude and a bit error rate of received signals to measure the performance of the antenna;

applying the bias to at least a portion of the at least one dielectric layer to improve at least one of the signal strength and bit error rate of the received signals.

7. The method of claim 1, further comprising:

applying a bias to a first portion of at least one dielectric layer to alter the performance of the antenna to achieve a first type of performance characteristics; and applying a bias to a different second portion of the at least one dielectric layer to alter the performance of the antenna to achieve a second type of performance characteristics.

8. An implantable medical device ("IMD"), comprising:

an antenna structure derived from at least one dielectric layer and an antenna; and a plurality of electrodes arranged with respect to the at least one dielectric layer for applying a bias across at least a portion of the at least one dielectric layer, wherein the electrodes are connected to a power source in the IMD;

a controller communicatively coupled with the antenna for sending and receiving telemetry signals, such that the controller is configured to:

measure a performance of the antenna based on certain characteristics of signals being received by the antenna; and cause a bias to be applied to at least a portion of the at least one dielectric layer by the plurality of electrodes to alter the performance of the antenna.

9. The implantable medical device of claim 8, wherein the at least one dielectric layer and the antenna are part of a monolithic antenna structure that has been co-fired together.

10. The implantable medical device of claim 8, wherein the at least one dielectric layer comprises a ceramic material.

11. The implantable medical device of claim 10, wherein the ceramic material comprises a low temperature co-fire ceramic (LTCC) material having a melting point between about 850 C.° and 1150 C.° and a cofireable paste having a high dielectric constant.

12. The implantable medical device of claim 10, wherein the ceramic material comprises a high temperature co-fire ceramic (HTCC) material having a melting point between about 1100 C.° and 1700 C.°.

13. The implantable medical device of claim 8, wherein the antenna structure is derived from a plurality of dielectric layers such that the antenna is embedded within the plurality of dielectric layers, further wherein the plurality of electrodes and antenna are formed on the same dielectric layer.

14. The implantable medical device of claim 8, wherein the antenna structure is derived from a plurality of dielectric layers such that the antenna is embedded within the plurality of dielectric layers, further wherein the plurality of electrodes and antenna are formed on different dielectric layers.

15. The implantable medical device of claim 8, further wherein the controller is further configured for applying the bias to the at least one dielectric layer in order to provide beam steering functionality to the antenna, such that signals communicated to and from the antenna can be selectably amplified.

16. The implantable medical device of claim 8, further wherein the controller is further configured for applying the bias to the at least one dielectric layer in order to provide beam steering functionality to the antenna, such that signals communicated to and from the antenna can be selectably attenuated.

17. The implantable medical device of claim 8, further wherein the controller is further configured for applying the bias in order to perform at least one of altering the gain of the signals received by the antenna or achieving impedance matching between the antenna and a propagation environment surrounding an implant location for the IMD.

18. An antenna structure for an implantable medical device ("IMD"), comprising:

a cofired monolithic structure derived from at least one dielectric layer and an antenna; and a plurality of electrodes arranged with respect to the at least one dielectric layer for applying a bias across at least a portion of the at least one dielectric layer, wherein the electrodes are connected to a power source in the IMD;

controller means for:

measuring a performance of the antenna based on certain characteristics of signals being received by the antenna; and causing a bias to be applied to at least a portion of the at least one dielectric layer by the plurality of electrodes to alter the performance of the antenna.

19. The antenna structure for an IMD of claim 18, wherein the controller means is further configured for applying the bias to the at least one dielectric layer in order to provide beam steering functionality to the antenna, such that signals communicated to and from the antenna are selectably amplified.

20. The antenna structure for an IMD of claim 18, wherein the controller means is further configured for applying the bias to the at least one dielectric layer in order to provide beam steering functionality to the antenna, such that signals communicated to and from the antenna are selectably attenuated.

21. The antenna structure for an IMD of claim 18, wherein the controller means is further configured for applying the bias in order to perform at least one of altering the gain of the signals received by the antenna or achieving impedance matching between the antenna and a propagation environment surrounding an implant location for the IMD.

22. The antenna structure for an IMD of claim 18, wherein the controller means is further configured for:

measuring at least one of a signal strength, error vector magnitude and a bit error rate of received signals to measure the performance of the antenna;

applying the bias to at least a portion of the at least one dielectric layer to improve at least one of the signal strength and bit error rate of the received signals.

* * * * *